United States Patent [19]
Kohler et al.

[11] Patent Number: 5,459,403
[45] Date of Patent: Oct. 17, 1995

[54] APPARATUS FOR DETERMINING THE MOISTURE CONTENT OF A MEDIUM

[75] Inventors: Kurt Kohler, Ettlingen; Robin Fundinger, Karlsbad, both of Germany

[73] Assignee: IMKO Micromodultechnik GmbH, Ettlingen, Germany

[21] Appl. No.: 238,004

[22] Filed: May 3, 1994

[30] Foreign Application Priority Data

Apr. 29, 1993 [DE] Germany .............................. 9306441 U
Oct. 12, 1993 [DE] Germany ......................... 43 34 649.9

[51] Int. Cl.⁶ ........................... G01R 27/02; G01R 31/11
[52] U.S. Cl. ......................... 324/643; 324/664; 324/533; 324/690; 340/604
[58] Field of Search ...................... 324/525, 532, 324/533, 534, 535, 643, 663, 664, 676, 689, 690, 694, 696, 149; 340/604

[56] References Cited

U.S. PATENT DOCUMENTS

| | | | |
|---|---|---|---|
| 2,373,846 | 4/1945 | Olken | 324/690 X |
| 3,105,214 | 9/1963 | Blythe et al. | 324/696 X |
| 3,766,471 | 10/1973 | Pullman | 324/709 X |
| 5,212,453 | 5/1993 | Koehler et al. | 324/664 |

Primary Examiner—Kenneth A. Wieder
Assistant Examiner—Diep Do
Attorney, Agent, or Firm—Klaus J. Bach

[57] ABSTRACT

In an apparatus for determining the material moisture of a medium by measuring the dielectric coefficient of the medium around a measuring probe, wherein the apparatus includes a signal generator providing to one end of the probe a pulse signal, the echo of which, when returning from the other end of the probe, is received by a receiver, and a timing device determining the time elapsed between the introduction of the pulse signal and the return of the echo, the probe consists of a body structure which has electrical signal conductors disposed on its surface.

12 Claims, 2 Drawing Sheets

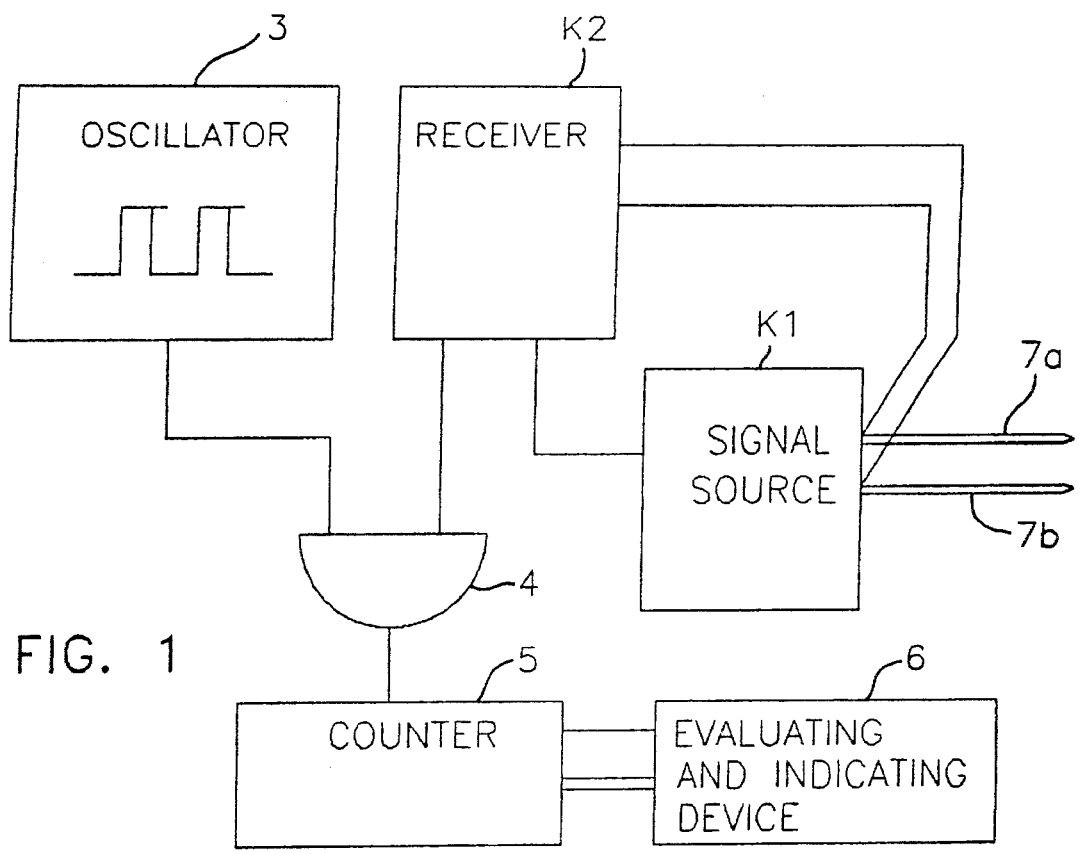
FIG. 1
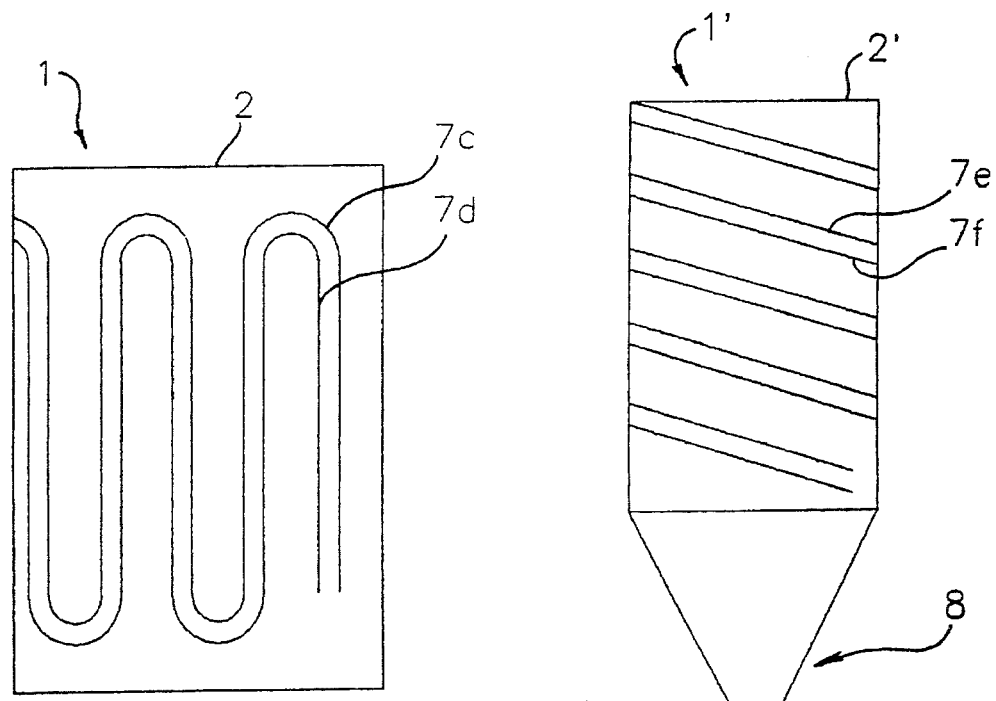
FIG. 2
FIG. 3

APPARATUS FOR DETERMINING THE MOISTURE CONTENT OF A MEDIUM

BACKGROUND OF THE INVENTION

The present invention relates to an arrangement for measuring the material moisture or a medium which forms the dielectric or a measuring conductor by determining its dielectric coefficient wherein, by means of a signal generator, a pulse signal is introduced into the measuring conductor at one end and, a receiver arranged at the same end receives the signal reflected from the other end or the measuring conductor and, in a time measuring device, the time elapsed between the start or signal introduction and reception or the reflected signal is determined.

Various methods and apparatus for determining the material moisture or a medium are known including chemical methods and electrical methods: For example, material moisture can be measured by way or measuring the electrical conductivity or the medium. Often this method is preferred because it requires only simple apparatus and can therefore be performed relatively inexpensively. It also permits continuous and practically delay-free measuring or the material moisture.

It is also possible to measure material moisture by determining the dielectric coefficient or the medium since there is a monotonic clear interrelation between the dielectric coefficient or a medium and its moisture content. The dielectric coefficient can be determined, for example, by means of an arrangement in which the medium to be measured is disposed between two plates and the inductive capacity of this arrangement is then determined. Such an arrangement, however, causes problems as to measuring procedures and the size of the capacitor plates is generally objectionable.

With the so-called echo method as disclosed in Applicant's U.S. Pat. No. 5,212,453 the above-referred to problems do not occur. The conductor takes the form of an open duct of finite length and known geometry. It has an electrical connection via which an electric pulse is introduced into the conductor and the time delay of the return of the echo from the end of the conductor is measured. It is known to provide the conductors in the form of two parallel needles which can be inserted into the medium to be measured. From the delay time of the echo the dielectric coefficient of the medium, and therefrom its moisture content, can be determined.

The needles however have to be relatively long in order to achieve high sensitivity, and because of the great length of the needles their utilization and handling is often somewhat complicated.

It is the principal object of the invention to provide an arrangement for measuring material moisture of this type which provides for high sensitivity and is also easy to handle.

SUMMARY OF THE INVENTION

In an apparatus for determining the material moisture of a medium by measuring the dielectric coefficient of the medium around a measuring probe, wherein the apparatus includes a signal generator providing to one end of the probe a pulse signal, the echo of which, when returning from the other end of the probe, is received by a receiver, and a timing device determining the time elapsed between the introduction of the pulse signal and the return of the echo, the probe consists of a body structure which has electrical signal conductors disposed on its surface.

Cylindrical bodies have been found to be particularly suitable.

In order to increase the length of the measuring conductor it may extend spirally around the body of the probe or it may be disposed meandrously on its surface. By such an arrangement the effective length of the measuring conductor can be made to be quite large without requiring the probe to be excessively large.

An arrangement with spiral conductors in which one of the conductors is wider than the other by a factor of 2 to 4, preferably 3, was found to provide for particularly good results. The different width of the conductors substantially increased the sensitivity and the accuracy of the probe. By the spiral arrangement of the conductors an error introduced as a result of a disadvantageous placement of the probe in the medium to be measured is essentially averaged out. As a result inaccuracies generated by arranging the probe, for example, within a tube disposed within the medium to be measured wherein the distance between the probe surface and the tube wall is not constant, are almost completely suppressed.

In another embodiment the probe is provided with an insulative coating which has a uniform dielectric coefficient. This protects the measuring conductor from mechanical damages without causing errors in the measuring results.

In a special embodiment of the invention the connections for the electrical conductors extend into the interior of the probe body. This can be achieved by providing bores in the probe body which extend radially inwardly and into which electrical connectors such as wires are then inserted. Within the probe body these connectors extend suitably axially outwardly. The probe body may be hollow or solid material. If appropriate a hollow probe body may be filled with a body of a different material selected so as to further improve the sensitivity and accuracy of the probe.

For measuring the moisture content of a medium a tube may be inserted into the medium which has an internal diameter slightly larger than the outer diameter of the probe. The probe is then inserted into the tube so that the probe can be easily removed from the medium in order to be replaced by another probe, for example. This makes it also possible to measure the moisture content at different locations within the medium by moving the probe within the tube to such different locations.

In a further embodiment the probe is provided with a pointed end so that the probe can be inserted directly into the medium to be measured without the use of a tube. For such a probe it is particularly advantageous if it is provided with the protective coating with uniform dielectric coefficient referred to above.

Further details, features and advantages of the arrangement according to the invention will become apparent from the following description making reference to the enclosed drawings.

BRIEF DESCRIPTION OF THE DRAWINGS

FIG. 1 shows generally the echo method utilized in connection with the present invention;

FIG. 2 shows a probe with signal conductors disposed meandrously on the surface thereof;

FIG. 3 shows a probe with spiral signal conductors and a pointed tip;

FIG. 4b is a top view of the probe shown in FIG. 4a, and

DESCRIPTION OF THE PREFERRED EMBODIMENTS

Figure 3A:
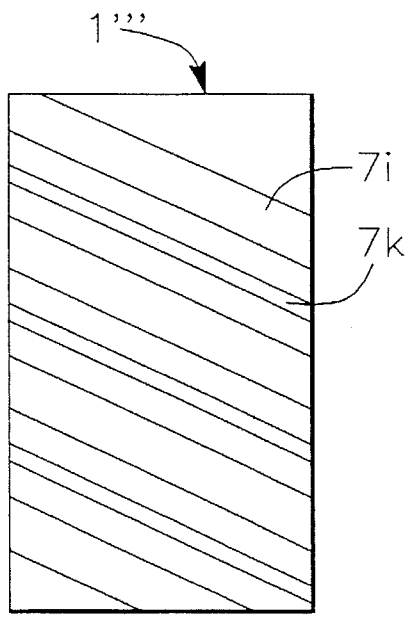
FIG. 3a shows a probe with spiral signal conductors of different width.

An arrangement for performing the echo method as shown in FIG. 1 includes an open-ended measuring structure having two parallel measuring rods 7a, 7b into which is introduced a voltage signal with as steep a ramp as possible generated by a signal source K1 which is connected to the measuring rods by supply lines of negligible length. The internal resistance of the signal source K1 corresponds to the wave resistance of the open-ended measuring rods 7a, 7b as far as it can be established with simple means for the center section of the measuring area. In this manner, with a suitable measuring range, only few interfering reflections are generated at the connection between the exit of the signal source K1 and the measuring rods 7a, 7b. At the ends of the measuring rods 7a, 7b full reflection occurs. The echo returns to the beginning of the measuring rods within a time which depends on the physical data of the measuring rods 7a, 7b as influenced by the moisture content of the dielectric material. By a receiver K2, which compares the voltage at the electrical connections of the measuring rods 7a, 7b with predetermined values, a gate signal for a counter 5 is generated which measures the time delay between the start of the energization of the rods and the return of the echo impulse by means of an independent oscillator 3. The counter 5 itself is connected to an analyzing and indicating device 6. The start of the gate opening can be delayed by the signal source K1 if this is advantageous so as to open the gate only after the signal reflection from the connections of the measuring rods is past.

As a result of different material moisture contents the dielectric coefficient and the capacity distribution in the medium which surrounds the probes 7a, 7b of the measuring arrangement differ. Since the geometric data of the measuring rods 7a, 7b are constant, there is a relation between the material moisture content and the measured delay-time of the echo. This can be given by an equation or a calibration curve Although satisfactory results have been achieved with the arrangement described above, it does have the disadvantage that the measuring rods 7a, 7b need to very long if a high sensitivity needs to be achieved and with such long measuring rods, handling of the arrangement is often difficult.

FIG. 2 shows a cylindrical probe 1 which has signal conductors 7c, 7d disposed thereon in a meandrous fashion. The signal conductors 7c, 7d are arranged at a distance from one another which de pends on the medium to be measured. As is quite apparent, as a result of the meandrous arrangement of the signal conductors 7c, 7d, their length is a multiple of the length which rods with a length of the height of probe 1 would have. As a result of the so-increased length of the signal conductors the sensitivity of the measuring arrangement is substantially increased.

FIG. 3 shows a cylindrical probe 1' with a lower pointed end 8. The pointed end facilitates insertion of the probe into a medium whose moisture content is to be measured. The body 2' of the probe 1' has spirally extending signal conductors 7e, 7f disposed on its surface. This measure also substantially increases the effective length of the signal conductors. For the protection from damage the probe is provided with an insulative coating with a uniform dielectric coefficient.

FIG. 3a also discloses a cylindrical probe 1''' with signal conductors 7i, 7k of different width. The different widths of the signal conductors provides for a substantial increase in the sensitivity and the accuracy of the probe. The spiral winding is particularly advantageous if the probe is inserted into the medium to be measured by way of a tube. The spiral winding provides for compensation of errors generated because the probe surface does not have the same distance from the tube wall all around its circumference and consequently also has different distances from the medium to be measured. If one winding portion is closely adjacent the tube surface at one side of the probe there is a larger distance at the opposite side which provides for compensation.

Figure 4A:
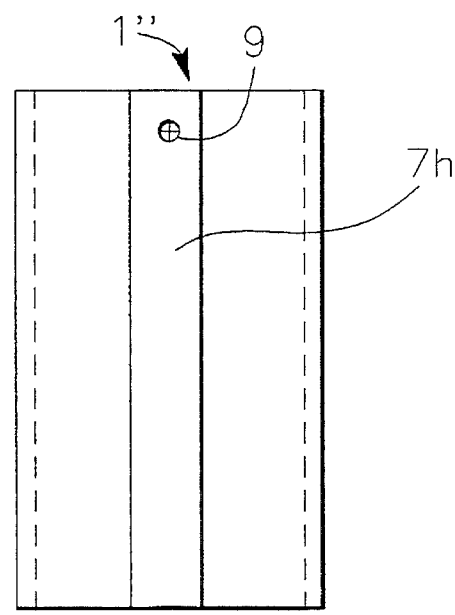
FIG. 4a is a front view of a probe with signal conductors arranged in parallel fashion.
Figure 4B:
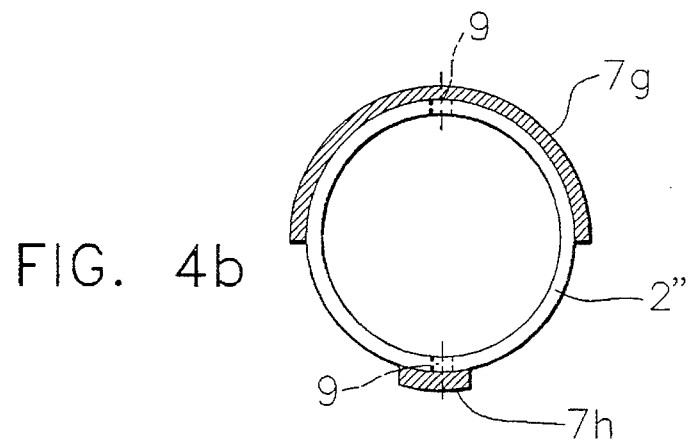

FIGS. 4a and 4b show a cylindrical probe 1'' which has disposed on its surface two signal conductors 7g, 7h. Both conductors 7g, 7h are parallel to one another in axial direction of the probe. The length of the conductor is almost the same as that of the cylindrical body 2''. One of the signal conductors 7g extends circumferentially for 180°, that is, it covers about half of the surface of the body 2''. The other signal conductor 7h is arranged on the cylinder surface of the probe radially opposite the one signal conductor 7g. Preferably it extends circumferentially For about 35°. This arrangement provides for a uniform distance between the longitudinal outer edges of the signal conductors 7g, 7h. The cylindrical body 2'' is hollow with openings 9 formed through the wall of the body 2'' in the vicinity of the signal conductors 7g, 7h. Electrical connecting wires may extend through the openings 9 in the area of the signal conductors 7g, 7h which provide for electrical connections to the signal conductors from the interior of the body 2''. The probes shown in FIGS. 3, 3a, 4a, and 4b are cylindrical and may be disposed in tubes which preferably have inner diameters that are about 1 mm larger than the outer diameter of the probes.

Notwithstanding the fact that the probes described above have cylindrical bodies 2, 2', 2'', the probe body may have a different shape if this is desirable. It may be triangular, rectangular, hexagonal or oval Also, the body 2, 2', 2'' may be hollow. It may also be Formed as a plate. It is important however that signal conductors are disposed on its surface in spaced relationship and that they are so oriented as to provide For maximum sensitivity.

Figure 5:
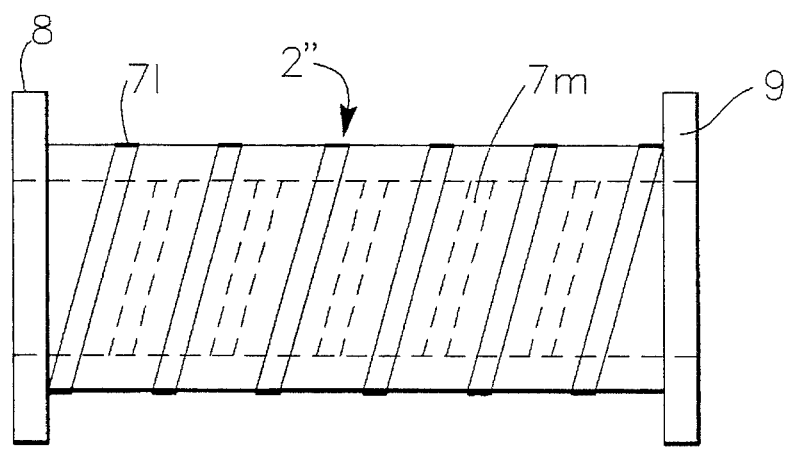
FIG. 5 shows a probe for installation in a conduit.

As shown in FIG. 5 the body 2'' is tubular and provided at its ends with mounting flanges 8 and 9 so that the probe can be installed in a conduit for measuring the moisture content of a medium flowing through the conduit, particularly of slurries flowing therethrough. Conductors 7l or 7m may be disposed on the outside or on the inside of the tubular probe. If they are disposed on the inside of the tubular body they are preferably covered with an insulative coating with a uniform dielectric coefficient.

What is claimed

1. An apparatus for determining the material moisture of a medium by measuring the dielectric coefficient of the medium around a measuring probe, said apparatus including a signal source for providing a pulse signal to one end of said measuring probe and a receiver connected at the same end of said measuring probe and receiving the echo of said signal when reflected and returning from the other end of said measuring probe and a counter for determining the time elapsed between the introduction of said signal into the measuring probe and the return of the echo reflected from the end of the measuring probe, said measuring probe having a body with electrical signal conductors disposed in the area of its surface and extending over said surface in a meandrous or spiral fashion so as to provide for a relatively long signal and return echo travel path resulting in an echo return delay providing for high measurement accuracy.

2. An apparatus according to claim 1, wherein said body is a cylinder.

3. An apparatus according to claim 1, wherein said electrical signal conductors are arranged so as to extend essentially in parallel relationship.

4. An apparatus according to claim 2, wherein said signal conductors extend on said body in axial direction and one of said signal conductors has a circumferential width of about 180° whereas the other signal conductor has a circumferential width of about 35°.

5. An apparatus according to claim 1, wherein one of said signal conductors has a width two to four times that of the other signal conductor, 6. An apparatus according to claim 1, wherein one of said signal conductors has a width three times that of the other signal conductor.

7. An apparatus according to claim 1, wherein said body includes electrical connections extending from the interior of said body to the signal conductors disposed on its surface for electrical connection therewith.

8. An apparatus according to claim 1, wherein said probe is provided with an insulative coating with uniform dielectric coefficient.

9. An apparatus according to claim 2, wherein, for performing said measurement, said probe is insertable into a tube which has an inner diameter which is 0.1 mm to 3 mm larger than the outer diameter of said probe.

10. An apparatus according to claim 9, wherein the inner diameter of said tube is 1 mm larger than the outer diameter of said probe.

11. An apparatus according to claim 2, wherein said probe is conical at its front with a pointed end.

12. An apparatus according to claim 1, wherein said probe is tubular and has mounting-flanges at its axial ends to facilitate mounting of said probe in a conduit carrying a medium whose moisture content is to be measured.

* * * * *